United States Patent [19]
Wingrove

[11] Patent Number: 5,800,458
[45] Date of Patent: Sep. 1, 1998

[54] COMPLIANCE MONITOR FOR MONITORING APPLIED ELECTRICAL STIMULATION

[75] Inventor: Robert C. Wingrove, Inver Grove Heights, Minn.

[73] Assignee: Rehabilicare, Inc., New Brighton, Minn.

[21] Appl. No.: 723,518

[22] Filed: Sep. 30, 1996

[51] Int. Cl.$^6$ ............................................. A61N 1/08
[52] U.S. Cl. ........................................ 607/2; 607/46
[58] Field of Search .......................... 128/905; 607/1, 607/2, 52, 58, 62, 63, 64, 46

[56] References Cited

U.S. PATENT DOCUMENTS

| | | | |
|---|---|---|---|
| 4,509,520 | 4/1985 | Dugot | 607/52 |
| 4,553,548 | 11/1985 | Varrichio et al. | 607/43 |
| 5,233,987 | 8/1993 | Fabian et al. | 607/41 |

OTHER PUBLICATIONS

Declaration of David Kaysen (signed Mar. 2, 1998).

*Primary Examiner*—William E. Kamm
*Assistant Examiner*—George R. Evanisko
*Attorney, Agent, or Firm*—Dorsey & Whitney LLP

[57] ABSTRACT

The present invention relates to a compliance monitor for use in a stimulator unit used in various devices to provide electrotherapy. The compliance monitor comprises a current sensing element, a controller, and a timer. The current sensing element is electrically connected to the controller, and the timer is operably connected to the controller. The current sensing element is located in the stimulator unit to monitor the current supplied through an output channel of the stimulator unit. When the current sensing element senses that current is supplied to through the output channel, the current sensing element outputs a signal to the controller. The controller upon receiving such a signal enables the timer to be started. When a stimulator unit provides a pulsating current, the controller has the capability to not stop the timer when the pulsating current is on a low cycle, during which period no current is being supplied to the patient.

28 Claims, 9 Drawing Sheets

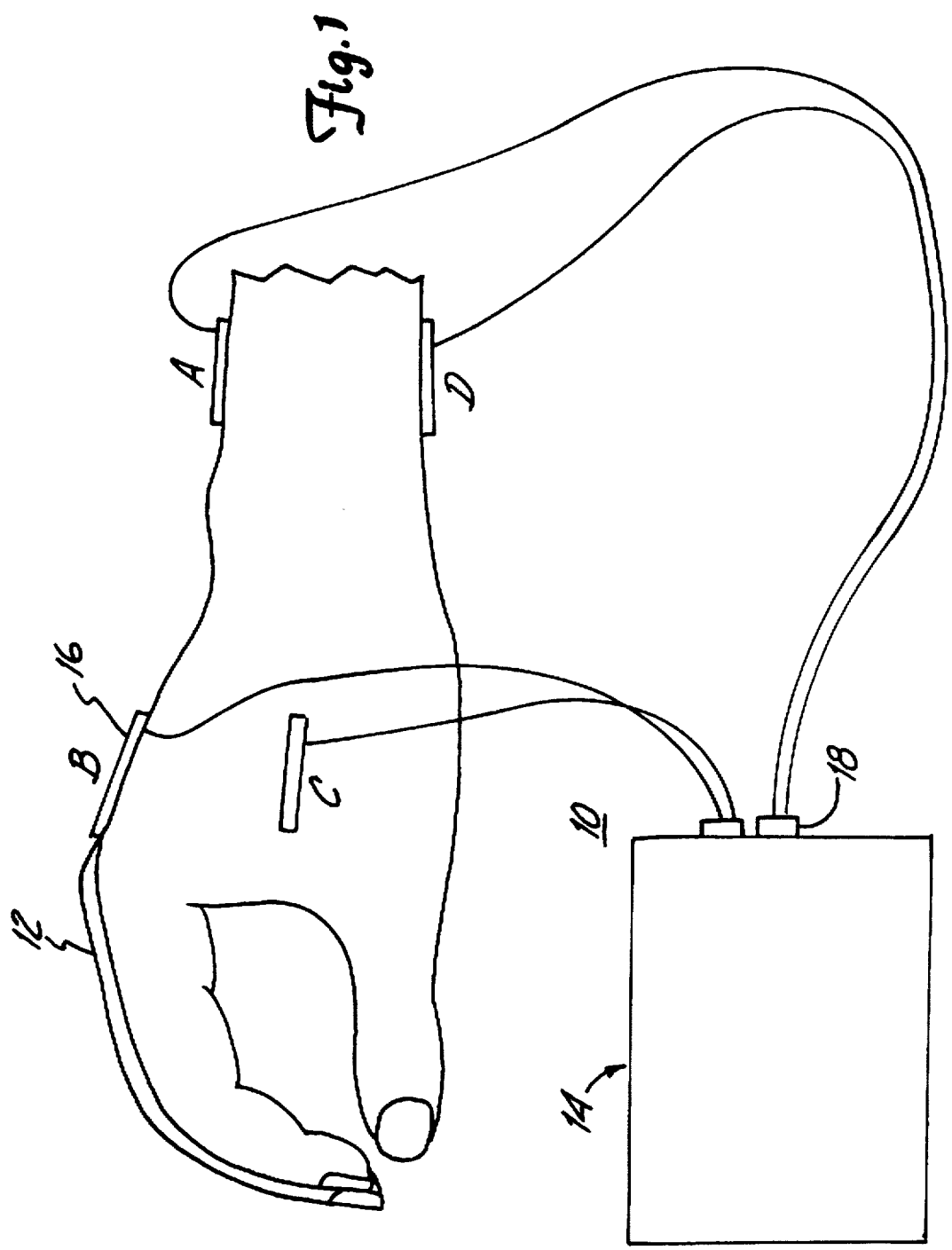

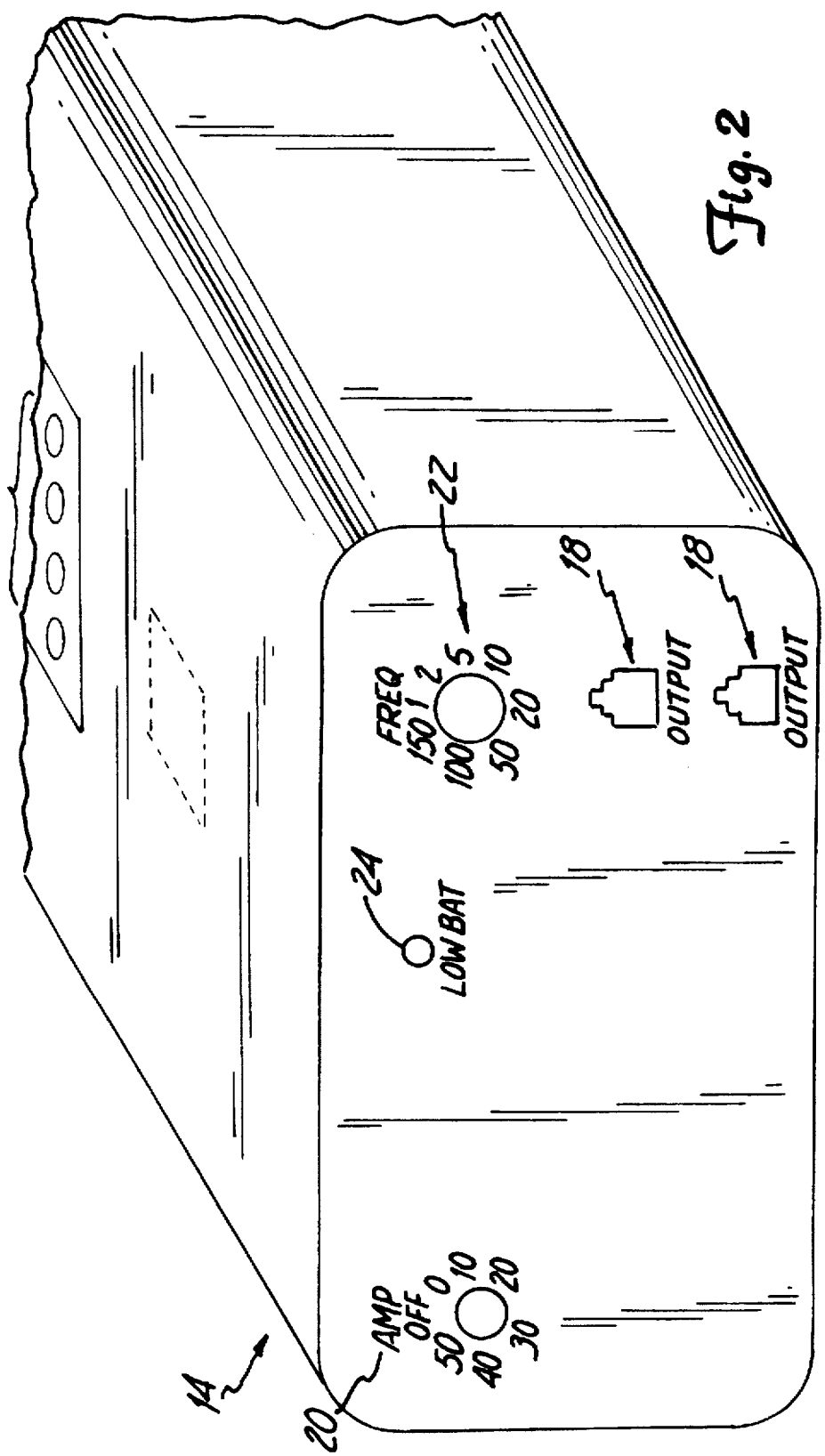

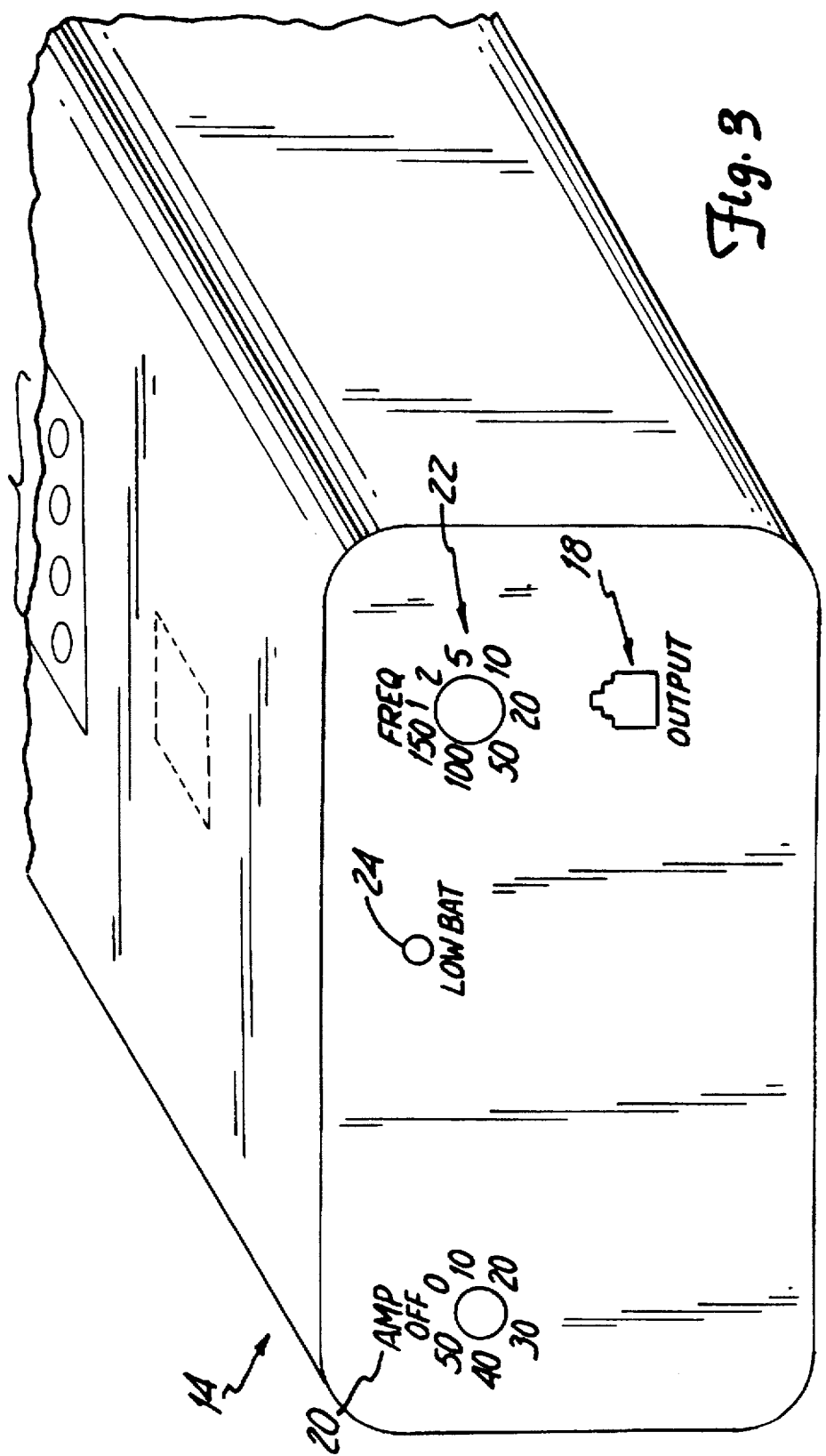

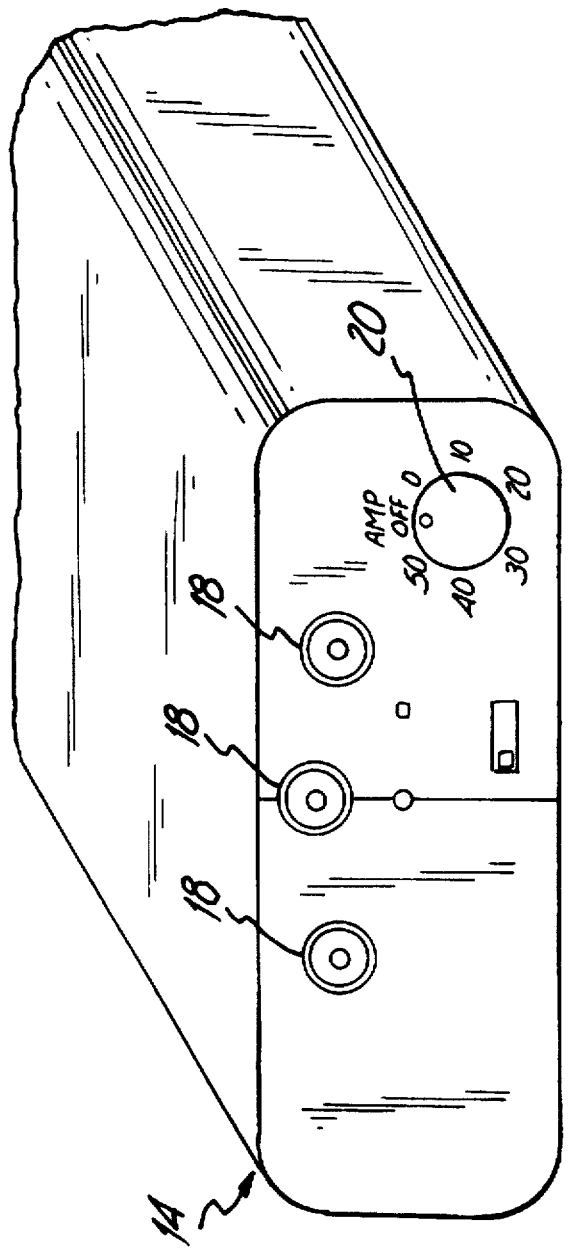

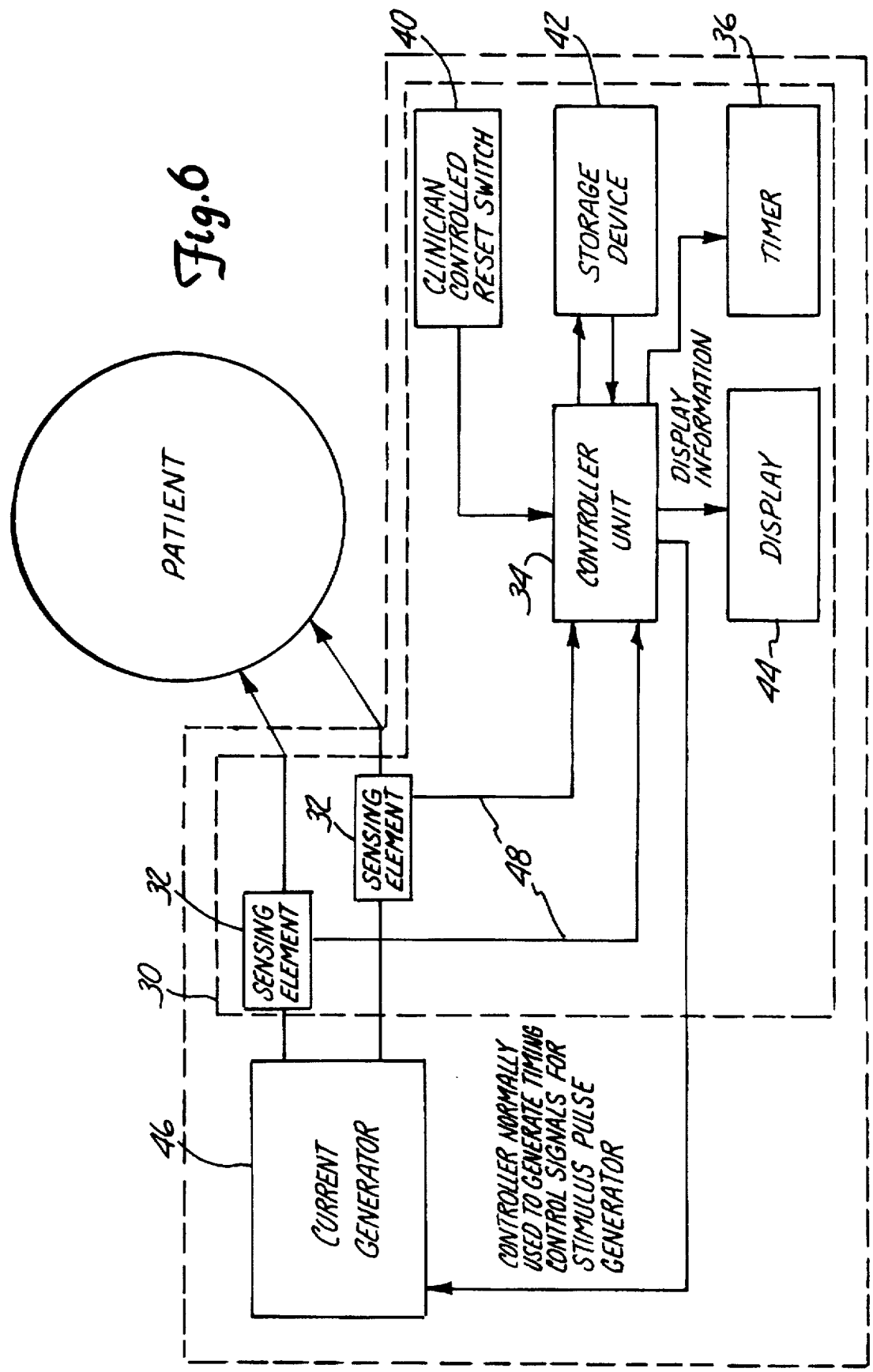

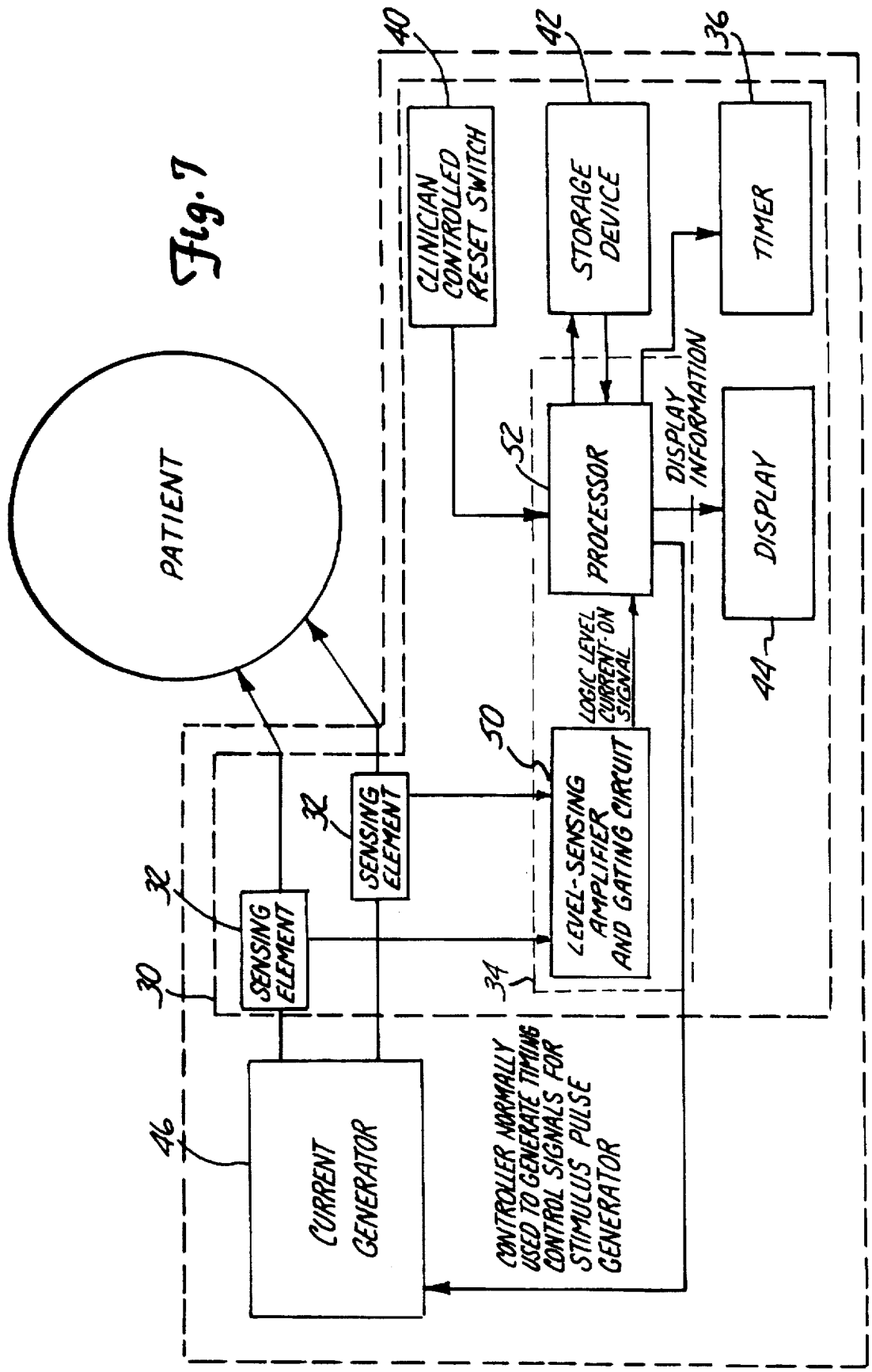

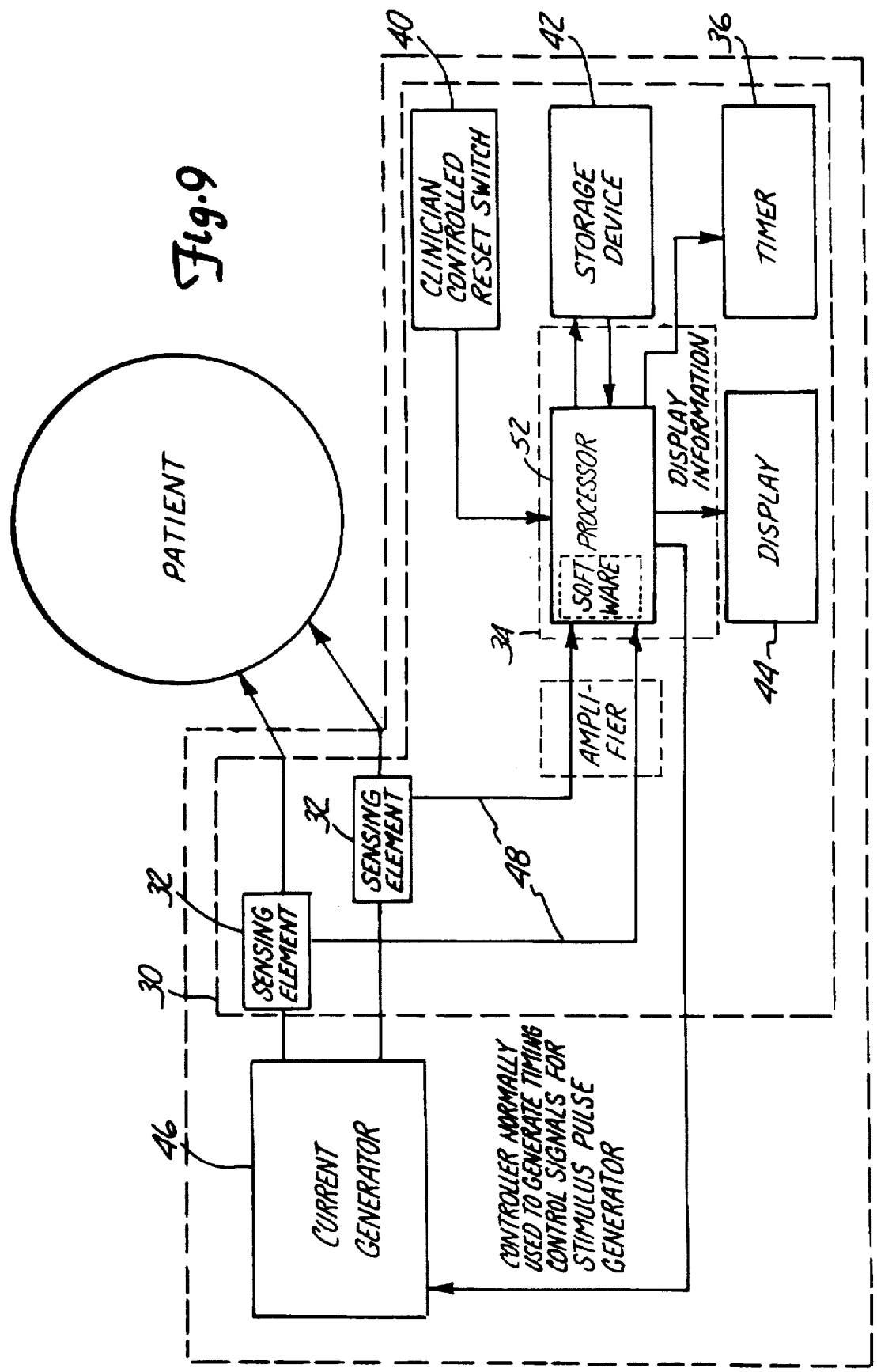

COMPLIANCE MONITOR FOR MONITORING APPLIED ELECTRICAL STIMULATION

TECHNICAL FIELD

The present invention relates to a device for monitoring the use of an electrical stimulator used to treat various medical conditions. In particular, the present invention relates to a circuit that monitors whether electrical stimulation is being provided to a user.

BACKGROUND OF THE INVENTION

Electrotherapy treatments which formerly were administered only in a clinical setting are now being prescribed for home use. Device miniaturization of the various treatment modalities such as high voltage pulsed galvanic ("HVPG"), interferential, neuromuscular stimulation (NMS), microcurrent, and transcutaneous electrical nerve stimulation (TENS) allow patients to continue treatments daily at home by self-application or with the help of family members.

Generally, an improvement in the recovery process results from daily treatments as opposed to the once or twice a week clinical treatments. However, just as with prescribed medication, the prescribing physician has little reassurance other than the patient's word that the treatment regimen has been followed. In some cases, the electrotherapy treatments provide a pleasant sensation and relieve pain. In such a case, one would expect a high level of patient compliance.

In cases where muscle strengthening and range-of-motion improvement are to be achieved by electrotherapy (i.e., such as recovery from joint surgery), the treatment may seem inconvenient, uncomfortable, and possibly painful. In this case, it is easy to understand why many patients would find reasons to drift away from the prescribed treatment regimen and not be entirely truthful when reporting to their doctor their actual use of the prescribed electrotherapy. Proper assessment of treatment results requires knowledge of the degree of patient compliance. In addition, reimbursement from insurance companies for the rental of the equipment may sometimes depend on proof of use of the equipment. Finally, an HMO or other payor may have a strong interest in compliance information.

Currently, some stimulators for use in providing electrotherapy being marketed have a means for displaying patient use time by accumulating and displaying the length of time that the stimulator is turned on. The problem with such monitoring devices is that while the stimulator is turned on, there is no assurance that the patient is receiving current from the stimulator. A device that would monitor whether electrical stimulation is being supplied is desirable.

An object of the present invention is to improve true patient compliance information by accumulating treatment time only when electrical stimulation is actually being delivered to the patient.

SUMMARY OF THE INVENTION

The present invention relates to a compliance monitor for use in a stimulator unit used in various devices to provide electrotherapy. The compliance monitor comprises a sensing element, a controller, and a timer. The sensing element is connected to the controller, and the timer is operably connected to the controller. The sensing element is located at an output channel in the stimulator unit to monitor the electrical stimulation supplied through the output channel of the stimulator unit. The sensing element outputs an stimulation indication signal which provides information on the level of electrical stimulation at the output channel. In response to this stimulation indication signal, the controller determines whether to increment the timer. When the sensing element senses that electrical stimulation is supplied through the output channel, the current sensing element outputs a current indication signal to the controller. The controller upon receiving such a signal increments the timer. When a stimulator unit provides a pulsating current as the electrical stimulation, the controller has the capability to not stop the timer when the pulsating current is on a low cycle, during which period no current is being supplied to the patient.

BRIEF DESCRIPTION OF THE DRAWINGS

FIG. 1 shows a stimulator unit connected to a brace which is attached to a flexing portion of the body.

FIG. 2 is a perspective view of a stimulator unit having two output channels.

FIG. 3 is a perspective view of a stimulator unit having one output channel.

FIG. 4 is a front plan view of a stimulator unit having two non-isolated output channels.

FIG. 6 is a block diagram of the compliance monitor and its interrelationship to the stimulator unit.

FIG. 7 is a block diagram of the compliance monitor showing the parts of the controller.

FIG. 9 shows another embodiment of the controller.

DETAILED DESCRIPTION OF THE PREFERRED EMBODIMENT

Figure 5A:
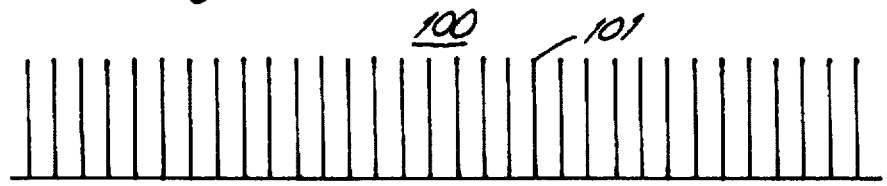
FIG. 5A–5D illustrates a constant current pulse train and high and low cycles of current pulses.

There are many medical devices using a form of stimulation to provide tissue treatment. As shown in FIG. 1, one such tissue treatment device is an electrotherapy unit 10 secured to a body portion 12. The electrotherapy unit 10 comprises a stimulator unit 14 and at least two electrodes 16 (as shown in FIG. 1, the unit 10 has four electrodes 16). The stimulator unit 14 will have at least one output channel 18. As shown in FIG. 1, the unit 10 has two output channels 18. A pair of electrodes 16 is electrically connected to one output channel 18. Electrical current is supplied to the body portion 12 through the electrodes 16 from the stimulator unit 14 via the output channel 18. The apparatus of the present invention is located within the stimulator unit 14 such that it is able to monitor electrical stimulation flowing through the output channel 18.

The stimulator unit 14 may be, among others, a neuromuscular stimulator ("NMS") unit, a transcutaneous electrical nerve stimulator ("TENS") unit, a high voltage pulsed galvanic stimulator unit, an interferential stimulator unit, or a microcurrent stimulator unit. The apparatus of the present invention is designed to be used with any type of electrical stimulator unit 14. Although the present invention will be described in terms of sensing current, the present invention could be used to sense voltage or other physical value representative of unit output by a stimulator unit 14.

With reference to FIGS. 2–4, various stimulator units 14 may be used with the present invention. FIG. 2 shows a typical stimulator unit which has two isolated output channels 18. Furthermore, as shown in FIG. 2, the stimulator unit 14 may have an amplitude control 20, a frequency control 22, and a low battery indicator 24.

FIGS. 3 and 4 show a stimulator unit 14 having a single output channel 18 and a stimulator unit 14 having two non-isolated output channels 18 respectively. In FIG. 4, the non-isolated output channels 18 share a common central electrode 19. As will be described later, the apparatus of the present invention may be used in these types of stimulator units 14 to determine the amount of time current is supplied to the user.

Before describing the compliance monitor, a brief description of the type of current produced through a stimulator unit 14 will be provided. A stimulator unit 14 can provide a continuous train of current pulses 100 (see FIG. 5A). When constant current is provided, the stimulator unit 10 monitors the current supplied and maintains the amount of current supplied through an output channel 18 at a constant level.

Figure 5B:
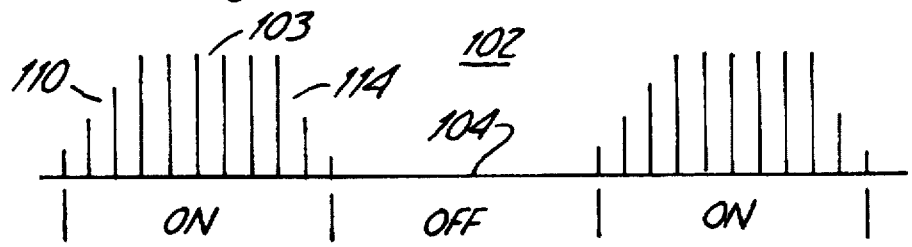
Figure 5C:
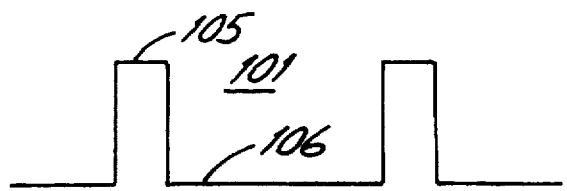
Figure 5D:
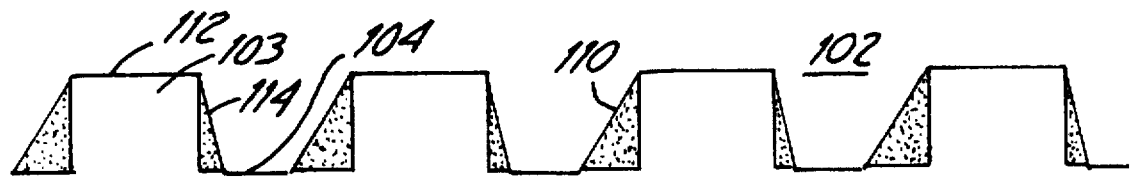

The stimulator unit 10 may also provide trains of interrupted current pulses 102. FIGS. 5B and 5D show a current pulse train 102 comprising a plurality of pulses 101 (see FIG. 5C). Pulse train 102 is comprised of alternating high cycles 103 and low cycles 104. The high cycle 103 of pulse train 102 has a ramp-up section 110, a peak current section 112, and a ramp-down section 114. Each high cycle 103 of pulse train 102 comprises a plurality of pulses 101. The pulses 101 vary in amplitude, and have a duration 105 and a pulse interval 106. Pulse duration 105 for most stimulators may range from as low as 5 microseconds in HVPG stimulators to as high as 1000 microseconds in some muscle stimulators. In the preferred embodiment the frequency for the pulses 101 is between 1 pulses/second to 4000 pulses/second inclusive. However, for purposes of this invention, the frequency of this pulse 101 must not be less than the frequency of the high cycle 103. During the high cycle 103 of a current pulse train 102, current is delivered to the user. During a low cycle 104, no current is delivered to user. In certain treatment procedures the low cycle 104 could be as long as 50 seconds to one minute. Usually, stimulators 14 that provide pulsatile constant current deliver 0 to 100 milliamperes into patient loads of 100 to 1000 ohms.

With reference to FIGS. 6, a compliance monitor 30 for a stimulator unit 14 supplying continuous train of current pulses 102 having two isolated output channels 18 will be described. FIG. 6 is a block diagram of a compliance monitor 30 located in a stimulator unit 14. The compliance monitor 30 comprises a sensing element 32, a controller 34, and a timer 36. The stimulator unit 14 houses a control reset switch 40 and a storage device 42, which are both operably connected to the controller 34. The stimulator unit 14 has two isolated output channels 18 through which a current generator 46 supplies current to the patient. The stimulator unit 14 also has a display device 44 for showing the amount of time the treatment has been received by the patient either on a cumulative basis or on a each discrete use basis.

As shown in FIG. 6, a sensing element 32 is located at each of the two isolated output channels 18. Each sensing element 32 outputs a stimulation indication signal 48, which indicates whether current is flowing through the channel 18 that the sensing element 32 is monitoring. Each sensing element 32 is connected to the controller 34 so that the controller 34 is responsive to the stimulation indication signal 48 output by the sensing element 32. In some cases, this stimulation indication signal 48 may need to be amplified for use by the controller 34.

In operation, when the stimulator unit 14 is turned on, each of the sensing elements 32 determines whether current is flowing in the channel 18 that it is monitoring. Based on the state of current flow within its channel 18, each sensing element 32 outputs to the controller 34 a stimulation indication signal 48. This stimulation indication signal 48 may need to be amplified if it is not strong enough for a controller 34 to use in determining whether current is flowing in the output channel 18. Based on the stimulation indication signal 48, the controller 34 determines whether to increment the timer 36. Each sensing element 32 constantly monitors an output channel 18 to determine whether current is flowing through the channel 18 it is monitoring. When current is flowing through the channel 18, the timer is incremented. Once current stops flowing through the channel 18, the controller 34 will not increment the timer 36. The amount of time elapsed during the treatment period may be stored in the storage device 42. Also, the amount of time elapsed may be displayed on the display device 44. The patient may use the control reset switch 40 to reset the timer 36.

When a stimulator unit 14 provides a train of current pulses 102, in order to accurately measure the total treatment time, the compliance monitor 30 must not stop incrementing the timer 36 during the low cycle 104 of the pulse train 102. Thus, even though during a low cycle 104 of the pulse train 102 there is no current flowing in the output channel 18, the compliance monitor 30 should not stop incrementing the timer 36 during treatment. Thus, the compliance monitor 30 of the present invention must design for this condition. Although in the preferred embodiment, the treatment time measured by the apparatus of the present invention includes the high cycle 103 and the low cycle 104, this present invention provides design parameters which allows it to be modified to apply appropriate measurement protocols based on the selected treatment protocol.

Figure 8:
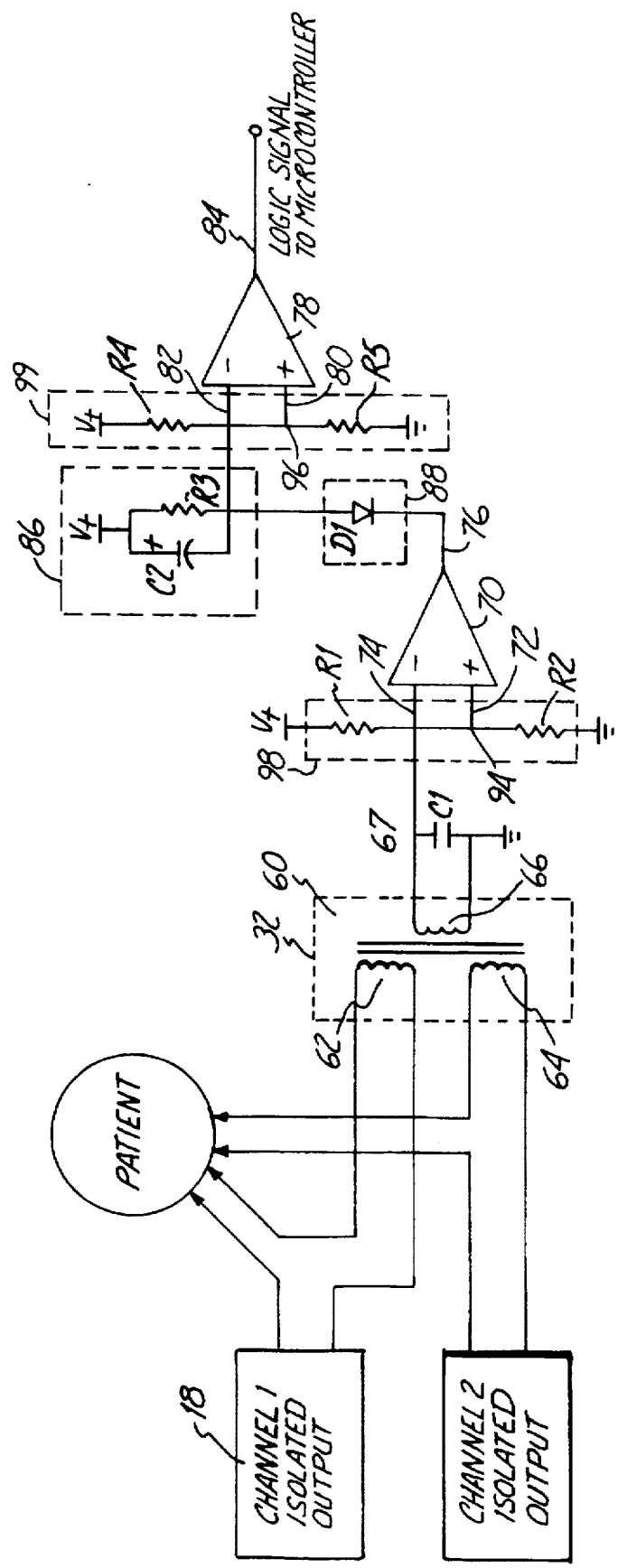
FIG. 8 is a schematic of the gating circuit in the controller.

With reference to FIGS. 7–8, a compliance monitor 30 for a stimulator unit 14 providing a train of pulses 102 will be described. FIG. 7 shows a block diagram of one embodiment of the compliance monitor 30 and its interrelationship to other parts of the stimulator unit 14. As shown in FIG. 7, there is a sensing element 32 monitoring each isolated output channel 18. The controller 34 comprises a level sensing amplifier and gating circuit 50 and a processor 52. The sensing element 32 is electrically connected to the level sensing amplifier and gating circuit 50. The level sensing amplifier and gating circuit 50 outputs a timer control signal, which allows the processor 52 to determine whether to increment the timer 36 or to not increment the timer 36. The processor 52 is connected to the timer 36, the control reset switch 40, the storage device 42, the display device 44, and the current generator 46, which supplies pulsed current.

With reference to FIG. 8, the detailed implementation of the sensing element 36 and the level sensing amplifier and gating circuit 50 will be described. FIG. 8 is a circuit diagram of the sensing element 32 and the level sensing amplifier and gating circuit 50. As shown in FIG. 8, the sensing element 32 is formed by a transformer 60. In the preferred embodiment, the sensing element 32 is a low-impedance, series sensing element. In order to satisfy these requirements, the transformer 60 used in the present invention comprises two isolated primary coil windings 62, 64 and a secondary coil winding 66. Each of the primary coil windings 62, 64 has eight (8) turns. The inductance of each of the primary coil windings 62, 64 is fifteen (15) microhenrys. The secondary coil winding 66 has thirty-two turns. This secondary coil winding 66 is connected in parallel to capacitor C1. This secondary coil winding 66 is also connected to the negative input of the first comparator at node 67.

Continuing to refer to FIG. 8, the level sensing amplifier and gating circuit 50 comprises a first comparator 70 having a positive terminal 72, a negative terminal 74 and an output 76, a second comparator 78 having a positive terminal 80, a negative terminal 82, and an output terminal 84, a time delay circuit 86, and a rectification circuit 88. As shown in FIG. 8, the output 76 of the first comparator 70 is connected to the rectification circuit 88. The rectification circuit 88 is connected to the negative terminal 82 of the second comparator 78 and the delay circuit 86 at node 92. The output terminal 84 of the second comparator 78 is connected to the processor 50. Each of the positive terminals 72, 80 is connected to one of nodes 94, 96 associated with one of first and second voltage dividing circuits 98, 99. The first voltage dividing circuit 98 comprises resistor R1 and R2. Resistors R1 and R2 are connected to each other and the positive terminal 72 of the first comparator 70 at node 94. The other terminal of resistor R1 is connected to the battery (or other power supply), and the other terminal of resistor R2 is connected to ground. The values of the secondary winding of the transformer and of resistors R1 and R2 are selected so as to have a sense threshold of five percent or less of the maximum output of the stimulator. Thus, based on the threshold set by the values of the resistors R1 and R2 in the first voltage dividing circuit 98, which determines the sensitivity to current of the first comparator 70, and the current indication signal 48 output by the current sensing element 32, the first comparator 70 outputs a signal which indicates whether current is flowing in a channel 18.

The second voltage dividing circuit 99 comprises resistor R4 and R5. Resistors R4 and R5 are connected to each other and the positive terminal 80 of the second comparator at node 96. The other terminal of resistor R4 is connected to the battery (or other power supply), and the other terminal of resistor R5 is connected to ground. The values must be chosen so that the controller 34 will increment the timer 36 during a low cycle 104 for a predetermined period of time, which defines the maximum amount of time a low cycle 104 can exist. However, if a particular treatment protocol requires a different time period measurement (e.g., not to include the entire low cycle), these values can be selected to allow for measurement of a treatment period in accordance with the treatment protocol.

With reference to FIG. 8, the time delay circuit 86 will also be described. The time delay circuit 86 comprises a capacitor C2 connected in parallel to a resistor R3. Values of C2 and R3 must be sufficiently large so that the voltage at the negative terminal 82 of the second comparator 78 remains below the voltage provided at the positive input of the second comparator by resistors R4 and R5 for a time in excess of the longest time period between output pulses of the stimulator. As described previously, for certain muscle stimulation treatments, the low cycles 104 of the pulse train 102 may be in excess of 30 or 40 seconds. Therefore, values for C2 and R3 may be as high as 10 microfarads and 10 megohms respectively. Thus, the time delay circuit 86 causes the output 84 of the second comparator 78, which is the timer control signal, to remain in a high state, thereby, providing accurate information regarding the amount of time the patient has been treated.

The rectification circuit 88 comprises a diode. This diode allows current to flow when the first comparator 70 outputs a low state through its output terminal 76. Otherwise, it prevents the flow of current to the first comparator 70.

In operation, the stimulator unit 14 is turned on and the current generator 46 provides a train of current pulses 102 through each of the output channels 18. During a high cycle 103 of the pulse train 102, the sensing element 32 senses current in the output channel 18 and outputs a current indication signal 48 to the first comparator 70. This input to the negative terminal 72 of the first comparator 70 causes the comparator's output to change from a high state to a low state. In the preferred embodiment, this change in output occurs during the ramp-up section 110 of the high cycle 103 of a pulse train 102. However, the values of resistors R1 and R2 may be manipulated such that the threshold value allows the first comparator 70 output to change at a selected level during the ramp-up section 110 of the high cycle 103 of the pulse train 102.

When the first comparator 70 outputs a low state, the diode 88 allows current to flow to the first comparator 70. When the output 76 of the first comparator 70 is in a low state, capacitor C2 begins charging. The timer control signal 85 output by the second comparator 78 via its output 84 to the processor 52 is in a high state. Based on the high state, the processor 52 increments the timer 36.

During some part of the ramp-down section 114 of the high cycle 103 of a pulse train 102 and during the low cycle 104 of the pulse train 102, the sensing element 32 senses a drop in the amount of current in the output channel 18. Thus, in the preferred embodiment, because of the values selected for resistors R1 and R2 (which sets the threshold voltage for the first comparator 70) the current indication signal 48 output by the current sensing element 32 to the negative input 72 of the first comparator 70 causes it to output a high state. Capacitor C2 begins to discharge through resistor R3. However, because of the values selected for capacitor C2 and resistor R3, the voltage at the negative input of the second comparator 78 remains below the voltage provided at the positive input 80 by resistors R4 and R5 for a time in excess of the longest time period between high cycles 103 of the pulse train 102 in of the stimulator 14. Thus, the timer control signal 85 output by the second comparator 78 through output 84 remains in a high state, and the processor 52 continues to increment the timer 36. If a high cycle 103 of the pulse train 102 does not occur within this predetermined period of time defined by the values of the second voltage dividing circuit 98 and the values of the components in the time delay circuit, the voltage at the negative input 82 of the second comparator 78 becomes greater than the voltage at the positive input 80 of the second comparator 78, thereby causing the timer control signal 85 output by the second comparator 78 through its output 84 to be in a low state. Based on this low state output, the processor 52 will stop incrementing the digital timer 36.

The processor 52 displays the time value on an LCD display. The total time information would also be stored in a non-volatile memory (EPROM) using methods well known to those skilled in the art. Thus, a physician can accurately determine the cumulative time the patient had treatment.

Alternatively, for constant current supplying stimulator units 14, the sensing element 32 may be the current sensor used in such units to maintain the constant current level. The output from the sensing element 32, which is used for feedback purposes in such units 14, may be by the controller 34 to determine the treatment period.

FIG. 9 shows a microprocessor based alternative embodiment. In this embodiment, the controller 34 is a processor 52. The processor 52 has computer software to control sampling of stimulation indication signal 48 as well as interpretation of these sampled signals. As shown in FIG. 9, the detection of the low cycle may be achieved via software operative on the processor 52. The processor 52 is responsive to the stimulation indication signal 48. Based on this signal 48, the processor 32 then determines whether current is flowing in a channel 18. If current is flowing in the channel 18, then the timer 36 is incremented. If current is not flowing in the channel 18, then the processor 52 continues to increment the timer 36 for a predetermined period of time. During that time, the processor 52 polls the sensing element 32 to determine whether the stimulation indication signal 48 indicates that current is flowing through the channel 18. If no current is sensed within the predetermined time period, the processor 52 stops incrementing the timer 36. However, if current is detected, then the processor 52 continues to increment the timer 36. Thus, with software, upon detecting the start of the low pulse 104 based on the stimulation indication signal 48 from the sensing element 32, the processor 52 can wait a predetermined period of time and again read the output from the sensing element 32 to determine if a high cycle 102 of the pulse train 102 has occurred.

The computer software on the processor 52 may be configured to sense selected treatment protocol waveform and to apply appropriate treatment period measurement protocol based on the treatment protocol waveform. Thus, the software may, if necessary, apply a different treatment period measurement protocol based on the type of waveform output by a stimulator unit 14 (e.g., based on the waveforms output by a NMS unit, a TENS unit, a high voltage pulsed galvanic stimulator unit, an interferential stimulator unit, or a microcurrent stimulator unit).

In the case of single channel or non isolated two channel stimulators, the transformer may be replaced with a simple small value resistor or parallel reversed diodes.

While various embodiments of the present invention have been described, it should be appreciated that various modifications may be made by those skilled in the art without departing from the spirit and scope of the present invention. Accordingly, reference should be made to the claims to determine the scope of the present invention.

What is claimed is:

1. A compliance monitor for monitoring electrical stimulation from a stimulator unit, comprising:
    (a) a sensing element for sensing the electrical stimulation, the sensing element providing a stimulation indication-signal;
    (b) a controller responsive to the stimulation indication-signal for determining when electrical stimulation is applied, wherein the electrical stimulation comprises at least one on-phase and at least one off-phase; and
    (c) a timer operably connected to the controller to monitor the amount of time electrical stimulation is applied wherein the timer monitors the amount of time the at least one on-phase and the at least one off-phase has been applied.

2. The compliance monitor of claim 1, wherein the sensing element is a low impedance sensing element.

3. The compliance monitor of claim 2, wherein the impedance of the sensing element is in a range of approximately one ohm to about ten ohms.

4. The compliance monitor of claim 3, wherein the sensing element is a transformer.

5. The compliance monitor of claim 3, wherein the sensing element is a resistor.

6. The compliance monitor of claim 1, wherein the stimulation unit includes at least one output channel for supplying the electrical stimulation and the sensing element is operably connected with the output channel.

7. The compliance monitor of claim 1, wherein the controller comprises:

(a) a level sensing and gating circuit electrically connected to the sensing element for receiving the stimulation indication-signal in order to determine when the electrical stimulation is applied, the level sensing and gating circuit providing a timer control signal to indicate when the electrical stimulation is being applied;
    (b) a processor electrically connected to the level sensing and gating circuit for receiving the timer control signal, whereby the processor activates the timer responsive to the timer control signal indicating that the electrical stimulation is being applied.

8. The compliance monitor of claim 7, wherein the electrical stimulation is in one of an on-phase and an off-phase and wherein the level sensing and gating circuit comprises:
    (a) a first comparator electrically connected to the sensing element to receive the stimulation indication-signal, and in response to the stimulation indication-signal, determine if the electrical stimulation is in the on-phase when it is being applied, wherein the first comparator provides an on-phase signal when the electrical stimulation is in the on-phase;
    (b) a second comparator electrically connected to the first comparator, the second comparator providing the timer control signal to indicate that electrical stimulation is being applied in response to receiving the on-phase signal;
    (c) a time delay circuit electrically connected to the first and second comparator to continue providing the on-phase signal to the second comparator for a predetermined time after the electrical stimulation transitions from the on-phase to the off-phase.

9. The compliance monitor of claim 8, wherein the first comparator provides an off-phase signal responsive to the electrical stimulation transitioning from the on-phase to the off-phase and wherein the level sensing and gating circuit further comprises a rectification circuit interposed between the first comparator and the time delay circuit for isolating the on-phase signal provided by the time delay circuit from the off-phase signal provided by the first comparator.

10. The compliance monitor of claim 1, wherein the controller comprises a processor electrically connected to the sensing element, wherein the stimulation indication-signal output by the sensing element is received by the processor to determine if the electrical stimulation is being applied, wherein the processor activates the timer in response to determining that the electrical stimulation is being applied.

11. The compliance monitor of claim 10, further comprising software means operative on the processor for:
    (a) receiving the stimulation indication-signal;
    (b) determining whether the electrical stimulation is being applied based on the stimulation indication-signal output by the sensing element;
    (c) polling the sensing element within a predetermined period of time to determine if electrical stimulation is being applied; and
    (d) controlling the timer based on steps (b) and (c).

12. The compliance monitor of claim 1, wherein the stimulator unit includes an output channel for supplying the electrical stimulation when it is applied, wherein the electrical stimulation comprises pulsed electrical current having a high cycle and a low cycle, the sensing element operably connected with the output channel to sense the pulsed electrical current.

13. A compliance monitor for monitoring at least one output channel of a stimulator unit to measure the amount of time electrical stimulation is being supplied by the at least one output channel, comprising:

(a) a sensing element operably connected with the at least one output channel for sensing the electrical stimulation supplied by the at least one output channel, the sensing element providing a stimulation indication-signal;

(b) a controller connected to the sensing element for determining whether electrical stimulation is being supplied by the at least one output channel in response to the stimulation indication-signal, wherein the electrical stimulation comprises at least one on-phase and at least one off-phase;

(c) a timer in electrical communication with the controller to measure the amount of time electrical stimulation is being supplied by the at least one channel, wherein the controller increments the timer in response to determining that electrical stimulation is being supplied by the at least one channel wherein the timer monitors the amount of time the at least one on-phase and the at least one off-phase has been applied.

14. The compliance monitor of claim 13 adapted to monitor the at least one output channel of the stimulator unit, wherein the electrical stimulation of the stimulation unit is a train of electrical pulses, wherein each pulse has a high cycle and a low cycle.

15. The compliance monitor of claim 14, wherein the sensing element is a low impedance sensing element.

16. The compliance monitor of claim 15, wherein the controller comprises a level sensing and gating circuit for ensuring the timer continues to be incremented during the low cycle of a pulse.

17. The compliance monitor of claim 16, wherein the level sensing and gating circuit comprises:

(a) a first comparator electrically connected to the sensing element to receive the stimulation indication-signal, wherein the first comparator outputs an on-signal during the high cycle of a pulse and an off-signal during the low cycle of a pulse when electrical stimulation is being supplied;

(b) a second comparator electrically connected to the first comparator for outputting a timer control signal to increment the timer in response to receiving the on-signal; and (c) a time delay circuit connected to the first and second comparators to provide to the second comparator the on-signal after the first comparator outputs an off-signal in place of an on-signal.

18. The compliance monitor of claim 17, wherein the gating circuit further comprises a rectification device interposed between the first and second comparators for isolating the on-signal provided by the time delay circuit from the off-signal outputted by the first comparator.

19. The compliance monitor of claim 13, wherein the controller comprises a microprocessor.

20. The compliance monitor of claim 19, wherein the timer is a clock within the microprocessor, whereby the clock is in electrical communication with the microprocessor.

21. The compliance monitor of claim 20, wherein computer software operative on the microprocessor performs the steps of:

(a) receiving the stimulation indication-signal from the sensing element;

(b) determining whether electrical stimulation is being supplied by the at least one output channel based on the stimulation indication-signal;

(c) polling the sensing element within a predetermined period of time to determine if electrical stimulation is being supplied by the at least one output channel; and (d) controlling the timer.

22. A compliance monitor for monitoring electrical stimulation from a stimulator unit, comprising:

(a) a transformer for sensing the electrical stimulation, the transformer providing a stimulation indication-signal;

(b) a controller responsive to the stimulation indication-signal for determining when electrical stimulation is applied; and (c) a timer operably connected to the controller to monitor the amount of time electrical stimulation is applied.

23. A compliance monitor for monitoring electrical stimulation from a stimulator unit, the electrical stimulation being in one of an on-phase and an off-phase, comprising:

(a) a sensing element for sensing the electrical stimulation, the sensing element providing a stimulation indication-signal;

(b) a controller responsive to the stimulation indication-signal for determining when electrical stimulation is applied; and (c) a timer operably connected to the controller to monitor the amount of time electrical stimulation is applied;

(d) wherein the controller comprises: (1) a level sensing and gating circuit electrically connected to the sensing element for receiving the stimulation indication-signal in order to determine if the electrical stimulation is applied, the level sensing and gating circuit providing a timer control signal to indicate when the electrical stimulation is being applied, and (2) a processor electrically connected to the level sensing and gating circuit for receiving the timer control signal, whereby the processor activates the timer responsive to the timer control signal indicating that the electrical stimulation is being applied;

(e) wherein the level sensing and gating circuit comprises: (1) a first comparator electrically connected to the sensing element to receive the stimulation indication-signal, and in response to the stimulation indication-signal, determines if the electrical stimulation is in the on-phase when electrical stimulation is being applied, wherein the first comparator provides an on-phase signal when the electrical stimulation is in the on-phase, (2) a second comparator electrically connected to the first comparator, the second comparator providing the timer control signal to indicate that electrical stimulation is being applied in response to receiving the on-phase signal, and (3) a time delay circuit electrically connected to the first and second comparator to continue providing the on-phase signal to the second comparator for a predetermined time in response to the electrical stimulation transitioning from the on-phase to the off-phase.

24. The compliance monitor of claim 23, wherein the first comparator provides an off-phase signal responsive to the electrical stimulation transitioning from the on-phase to the off-phase and wherein the level sensing and gating circuit further comprises a rectification circuit interposed between the first comparator and the time delay circuit for isolating the on-phase signal provided by the time delay circuit from the off-phase signal provided by the first comparator.

25. A compliance monitor for monitoring at least one output channel of a stimulator unit to measure the amount of time electrical stimulation is being supplied by the at least one output channel, wherein the electrical stimulation supplied by the at least one output channel is a train of electrical pulses, the compliance monitor comprising:

(a) a low impedance sensing element operably connected with the at least one output channel for sensing the electrical stimulation supplied by the at least one output channel, the sensing element providing a stimulation indication-signal;

(b) a controller connected to the sensing element for determining whether electrical stimulation is being supplied by the at least one channel in response to the stimulation indication-signal;

(c) a timer operably connected to the controller to measure the amount of time electrical stimulation is being supplied by the at least one channel, wherein the controller increments the timer in response to determining that electrical stimulation is being supplied by the at least one output channel wherein the electrical stimulation comprises at least one on-phase and at least one off-phase.

26. The compliance monitor of claim 25, wherein the controller comprises a level sensing and gating circuit for ensuring the timer continues to be incremented during the low cycle of a pulse.

27. The compliance monitor of claim 26, wherein the level sensing and gating circuit comprises:

(a) a first comparator electrically connected to the low impedance sensing element to receive the stimulation indication-signal, wherein the first comparator outputs an on-signal during the high cycle of a pulse and an off-signal during the low cycle of a pulse when electrical stimulation is being supplied;

(b) a second comparator electrically connected to the first comparator for outputting a timer control signal to increment the timer in response to receiving the on-signal; and (c) a time delay circuit connected to the first and second comparators to provide to the second comparator the on-signal after the first comparator outputting an off-signal in place of an on-signal.

28. The compliance monitor of claim 27, wherein the gating circuit further comprises a rectification device interposed between the first and second comparators for isolating the on-signal provided by the time delay circuit from the off-signal outputted by the first comparator.

* * * * *